(12) United States Patent
Freeman

(10) Patent No.: US 6,969,489 B2
(45) Date of Patent: Nov. 29, 2005

(54) MICRO ARRAY FOR HIGH THROUGHOUT SCREENING

(75) Inventor: Alex Reddy Freeman, Plano, TX (US)

(73) Assignee: Cytoplex Biosciences, Plano, TX (US)

( * ) Notice: Subject to any disclaimer, the term of this patent is extended or adjusted under 35 U.S.C. 154(b) by 454 days.

(21) Appl. No.: 09/939,087

(22) Filed: Aug. 24, 2001

(65) Prior Publication Data

US 2003/0039585 A1 Feb. 27, 2003

(51) Int. Cl.[7] .......................... B01L 3/02; B01L 11/00; B01L 3/00; G01N 15/06; G01N 35/00
(52) U.S. Cl. ........................ 422/100; 422/50; 422/55; 422/63; 422/68.1; 422/81; 422/82; 422/101; 422/102; 422/103; 422/104; 436/43; 436/52; 436/53
(58) Field of Search ................ 422/50, 55, 63, 422/68.1, 81, 82, 100, 101, 102, 103, 104; 436/43, 52, 53; 438/14, 16, 17, 22, 48; 29/592, 592.1

(56) References Cited

U.S. PATENT DOCUMENTS

| | | | |
|---|---|---|---|
| 4,855,240 A | 8/1989 | Rosenstein et al. | |
| 5,354,692 A | 10/1994 | Yang et al. | |
| 5,529,756 A | 6/1996 | Brennan et al. | |
| 5,879,632 A * | 3/1999 | Demers | 422/100 |
| 5,882,930 A | 3/1999 | Baier | |
| 5,916,428 A | 6/1999 | Kane et al. | |
| 5,980,704 A | 11/1999 | Cherukari et al. | |
| 5,986,679 A | 11/1999 | Fassler et al. | |
| 6,063,260 A | 5/2000 | Olesen et al. | |
| 6,090,251 A | 7/2000 | Sundberg et al. | |
| 6,093,296 A | 7/2000 | Soane et al. | |
| 6,103,199 A * | 8/2000 | Bjornson et al. | 422/100 |
| 6,103,537 A | 8/2000 | Ullman et al. | |
| 6,110,426 A | 8/2000 | Shalon et al. | |
| 6,156,178 A | 12/2000 | Mansfield et al. | |
| 6,176,962 B1 | 1/2001 | Soane et al. | |
| 6,251,343 B1 * | 6/2001 | Dubrow et al. | 422/102 |
| 6,284,113 B1 * | 9/2001 | Bjornson et al. | 204/453 |
| 6,399,396 B1 * | 6/2002 | Bass | 436/180 |
| 6,454,924 B2 * | 9/2002 | Jedrzejewski et al. | 204/601 |
| 6,485,690 B1 * | 11/2002 | Pfost et al. | 422/102 |
| 6,689,323 B2 * | 2/2004 | Fisher et al. | 422/100 |
| 6,706,538 B1 * | 3/2004 | Karg et al. | 436/180 |

* cited by examiner

Primary Examiner—Jill Warden
Assistant Examiner—Brian Sines

(57) ABSTRACT

Array based fluid is stored in through holes that extend through a substrate. Combined capillary and hydrophyllic forces are used to retain the fluid and also transfer it to other substrates of similar type. In another embodiment vacuum and pressure forces are used to introduce the fluid and remove the fluid from the known through holes and transfer the remaining fluid to other substrates. In yet another embodiment, electrokinetic forces are used to retain and move the fluids across the substrates via the through holes. The substrates are aligned and the fluids are transferred or mixed based on the above techniques.

55 Claims, 8 Drawing Sheets

Fig. 1A

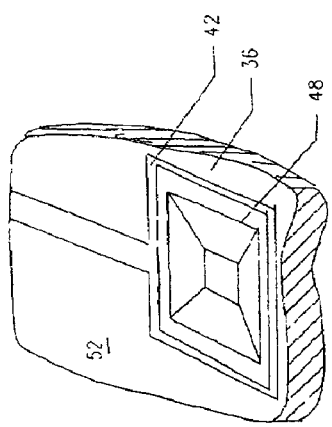
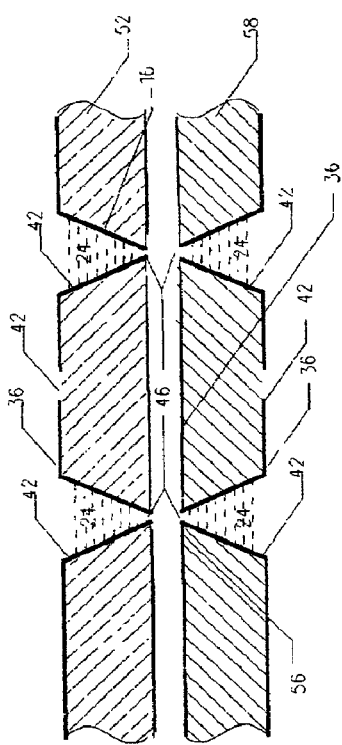
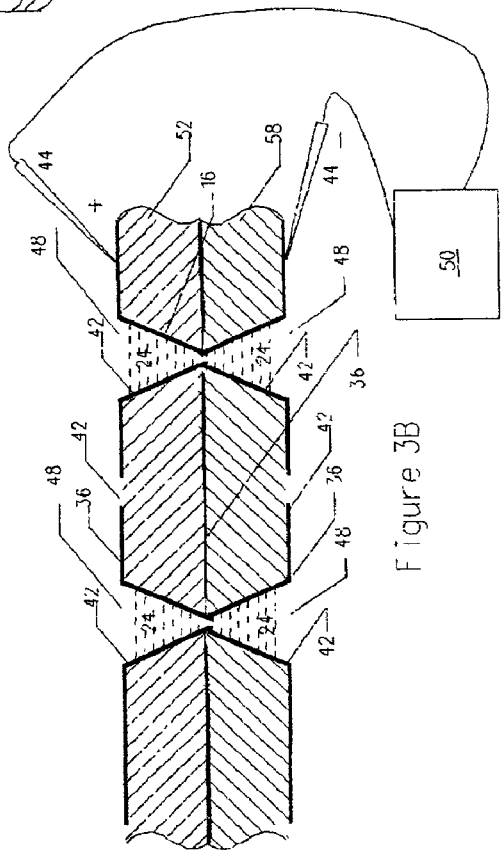

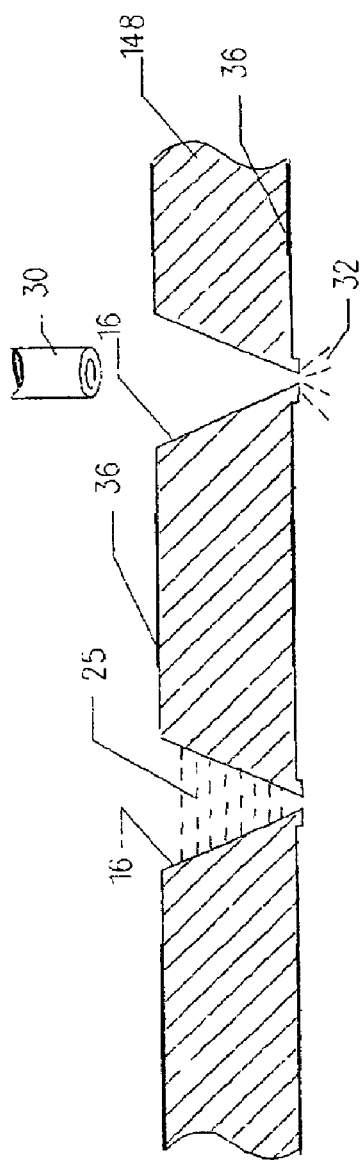
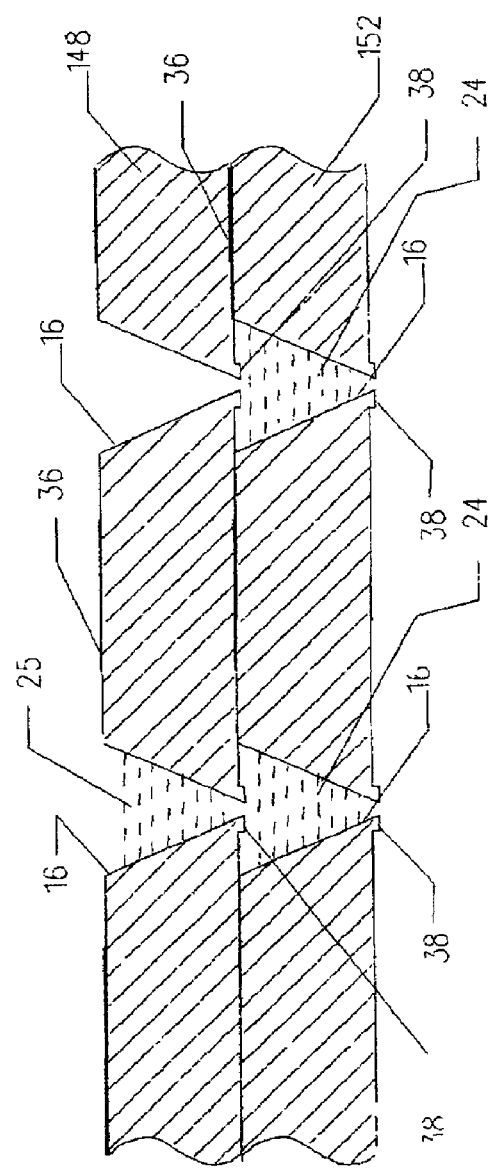
Figure 7A
Figure 7B

MICRO ARRAY FOR HIGH THROUGHOUT SCREENING

TECHNICAL FIELD OF THE INVENTION

This invention relates generally to micro arrays and microfluidics and more specifically to a system for forming arrays with fluids for high throughput screening, and combinatorial synthesis.

BACKGROUND OF THE INVENTION

Both homogenous and heterogeneous assays need to be performed in the current high throughput screening protocols. A universal platform for both homogenous and heterogeneous assays does not exist in the high density and ultra high density arrays. This does exist in the low-density modes such as 96 wells, 384 wells, 1536 wells. Beyond that, liquid dispensing adds exponential cost to the system design total cost. The current approach relaxes the positional accuracy and dispense accuracy needed to build high density liquid and spot array.

Over the years, the pharmaceutical industry has migrated to the parallel approach of screening compounds to find the drug candidates. This is typically called high throughput screening since, the density of parallel screening has gone from 96 wells to 384, and 1536 wells. Currently, the 96 and 384 wells are the most popular formats, where 96 or 384 simultaneous and independent experiments are carried out. These wells require assay volumes in the range of 1 to 500 microliters. Typically 4 or 8 dispenser heads dispense the liquids into the 96 or 384 wells. Various dispensing methods are currently available. The conventional fluid pump based, air compression based systems, piezoelectric and inkjet printing systems are commercially available. These systems are retrofitted with robotic plate handlers, fluorescent scanning readers to fit a wide range of homogenous and heterogeneous assays.

So far, the efforts to increase the density of the wells has reached 9640 wells and the higher increase in density has lead to considerable dispensing problems. The problems associated when the well density goes up are first, the positional accuracy of the dispensing systems has to go up to accommodate the increase in well density. Second, the problem of accurate dispensing to the nanoliter becomes very critical. Third, evaporation of the fluid becomes a dominant issue. Fourth, the surface to volume ratio of the wells increases and surface chemistry and surface properties strongly influence the dispensing accuracy.

These factors make the HTS (high throughput screening) and UHTS (ultra-high throughput screening) systems very expensive. In order to make the UHTS possible, novel dispensing methods have to be adapted. So far no effective method has evolved that can address the needs of both homogenous and heterogeneous assays. Various assay protocols exist for protein-protein binding, ligand-receptor binding, cell based assays, DNA hybridization etc. All these assay protocols fall into either homogenous or heterogeneous assays. Homogenous assays require one step addition of all the fluids. Heterogeneous assays require multiple fluid steps with intermediate wash steps. Currently there exists no universal platform for performing both homogenous and heterogeneous assays without requiring very expensive nano dispensing systems. The spot density of the dispenser is also very limited.

Currently pin based dispensing and thermal, hydraulic and acoustic fluid dispensing is used extensively to build arrays. For example, U.S. Pat. No. 6,090,251 by Sundberg et al., Jun. 18, 2000 covers use of array of pins to introduce liquids in open channels and the use of posts to withdraw the fluids from the channels. The major draw back of this particular technique is that the fluid volume cannot be precisely controlled because the volume depends on the surface tension, gravity and surface chemistry of the pins and the posts. Since the fluid is outside the pin or post, large evaporative losses occur, and control of the larger fluid volume with a much smaller surface area of the pin presents control problems especially if the pin diameter has even minor variations. This problem has been overcome in the present invention where the the inner surface of the through holes are used for dispensing the fluids, where the inter surface has much larger area than the surface area of the pin. In addition, the fluid bottom surface cross section has to be larger than the channel opening size, and hence imposes precise alignment requirements. This patent also shows a method of using planar electrophoresis for moving the fluid through the channel opening. The difficulty of this approach is that, the 2-D field moves the fluids in-plane of the substrate, but the fluid in the channel has to move in the third direction perpendicular to the substrate, presenting non ideal situation. Especailly in Microsystems, fluids are known to have very low Reynold's numbers which means, fluids can move as sheets, with very little motion transfer between the sheets which would exacerbate the problem of needed motion across the sheets.

Other drabacks of the general pin based arrays is that the dispensing array is not of high density and hence precision robotics and alignment systems are needed to build a large library of array. The dispensing array density matching the spotting array density is impractical to build. Building a pin density and pitch matching the spotting array density is very difficult. In addition, pins cannot transport larger quantity of fluids.

Capillary approch to moving fluids on substrates both laterally on substrates and perpendicularly through the substrate is particularly not new since this has been used in U.S. Pat. No. 4,855,240, Rosenstein et al., Aug. 8, 1989, U.S. Pat. No. 5,354,692, Yang et al., Oct. 11, 1994 and other patents. What is new in the current patent is the approach of combining arrays of through holes such that parallel fluid movement occurs under various physio-chemical conditions including electrokinetic forces. Gradients of these forces are another novelty of the current invention, where the gradient is created by combining in novel ways the differently prepared substrates.

SUMMARY OF THE INVENTION

It is therefore, an object of this invention to provide a system to dispense or transfer array of small volume samples by capillary, electrokinetic or vacuum based approach. It is further objective to retain the fluids inside the micro array by capillary and surface tension forces.

The additional objective of the current invention is to combine arrays of samples on one substrate to arrays of samples on a different substrate without requiring to transfer the samples individually.

The further objective is to move samples from one array to another array directly atop or beneath it, by electrokinetic forces and pneumatic forces.

The further objective is to combine the multiple substrate arrays into a single microwell.

The further objective is to combine substrates with the array to spot other substrates.

Further objective is to reduce the volume of reagents and compounds needed for assay.

It is additionally an object of the current invention to increase the number of tests that can be done in parallel.

It is the objective of the current invention by decreasing the sample volume, decrease the time to complete an assay or synthesis reaction.

It is the objective of the current invention to decrease the total cost of the tests per the individual element of the array.

The present invention takes advantage of the property that as fluid dispensing is miniaturized, surface forces play a dominant role in controlling the dispense volume and forces such as capillary force, gravitational force, surface charge force and surface adhesion forces interact with each other determining the final outcome of the fluid motion. Understanding these forces can lead to efficient nano dispensing systems for high throughput and ultra high throughput drug discovery.

In a first aspect, the present invention provides a microfluidic array comprising bottomless through holes etched in a substrate. The geometry of the through holes is optimized from multiple aspects. The first aspect is that the geometry allows capillary forces to retain the fluid sample inside the through hole. The second aspect is the geometry allows gradients in electric field intensity, which allows fluid motion through the through holes. The third aspect of the geometry optimization is that the fluid miniscus between two substrates need to contact each other before the capillary forces of one through hole can affect the fluid in the other through hole. This is done by etching collar like structures to position the protrusion of one substrate in the recess of the other substrate. Also by keeping the hydrophobic outside coatings to encircle the through holes in the middle, with 5–500 micron gap between the edges of the through hole opening and the hydrophobic coating opening.

BRIEF DESCRIPTION OF THE DRAWINGS

FIG. 3 is a cross sectional view of moving fluids from one through hole to another through hole which is directly next to it, by electrokinetic forces applied by an external power source.

FIGS. 7A and B is the cross sectional view of removing the plug of fluid in the through hole with an air jet and further transsffering the remaining plugs of fluids in the through holes to another substrate by capillary action.

DETAILED DESCRIPTION OF THE INVENTION

Figure 1:
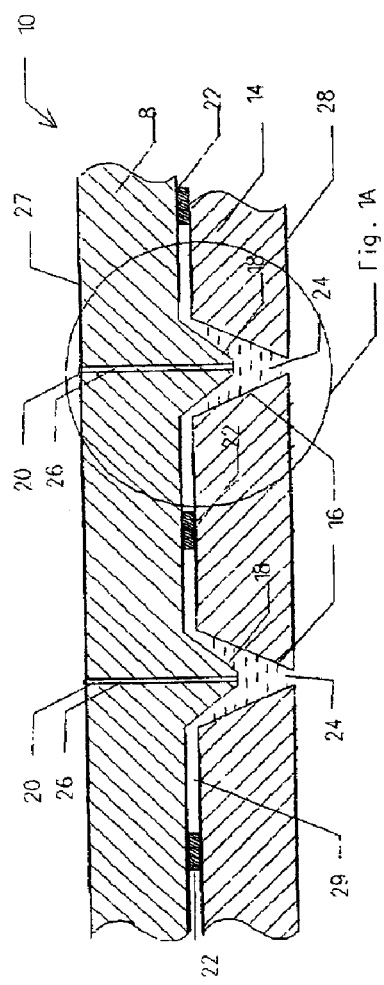
FIG. 1 is a cross sectional view of a typical microfluidic system in which fluids are drawn by capillary action from the top capillary to the bottom capillary.
Figure 1A:
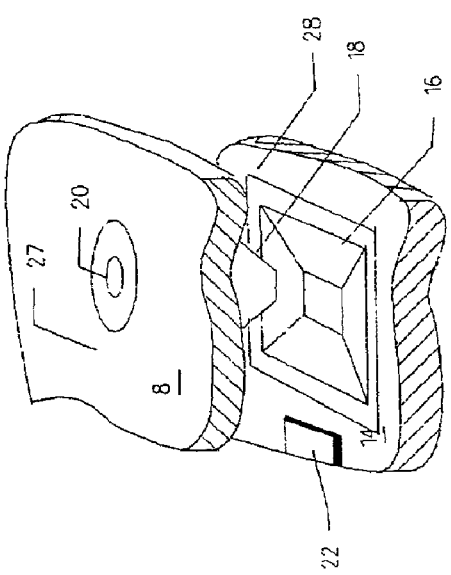

The microfluidic system 10 includes a substrate 14 having an array of through holes 16 as illustrated in FIG. 1. This substrate is any of the various materials such as silicon, quartz, glass, and plastics of cross linked and non crosslinked structures. The manufacturing method is described more in detail in the manufacturing issues section. Fluid samples and reagents 24 are introduced into the through hole arrays 16 by various physical and chemical means such as capillary action, meniscus contact between two fluid surfaces, pressure induced filling, vacuum induced suction, hydrophobic-hydrophilic induced forces and electrokinetic forces. The fluid samples 24 stays in place in the through holes due to capillary action and surface tension. Additional fluids 26 are introduced into the through hole array 16 by the capillary tubes 20 disposed in a second substrate 8, where the ends of the tubes 20 terminate in tapered protrusions 18. The microfluidic system 10, as shown in FIG. 1 and 1A, the first substrate, 8 consists of at least one peak, 18 protruding from the second surface of the substrate. The through-hole, 20 of the first substrate is in fluid communication with the tip of the peak, 18.

As shown in FIG. 1 and 1A, the microfluidic throughholes, 20 of the first substrate, 8 each reach the second surface at a peak, 18 protruding therefrom. The peak, 18 of the first substrate is operable to be partially accommodated within the microfluidic through-hole, 16. Each peak, 18 of the first substrate, 8 is operable to be at least partially accommodated within the microfluidic through-hole, 16 of the second substrate, 14 to make contact with the liquid, 24 retained therein. Protrusion 18 aligns substantially with through holes 16. In a preferred embodiment, top openings of through holes 16 are larger in diameter than the bottom openings of the through holes. Thus, through holes 16 may have conically tapered walls. The layer top openings of the through holes are sized and aligned to receive protrsions 18. Depending on the surface conditions, various fluid kinetics can occur. If the surface of the through hole 16 is hydrophilic, and the surface of tubes 20 hydrophobic, fluid 26 from tubes 20 moves into fluid 24 in 16 if the volume of through hole 16 can take the additional fluid. Only the amount of fluid that can fill up the volume of through hole 16 would be transferred. This fluidic motion causes both diffusive and laminar flow based mixing. Due to the laminar flow of 26 into 24, mixing times are dramatically short. If tube 20 is empty and the surface is hydrophilic and the surface of through hole 16 is hydrophobic, fluid 24 in 16 moves into the through hole 20 and fills up the volume of 20. This operation is due to the capillary forces in through hole 20, which moves the fluid from the through hole 16. If both the through holes 16 and 20 are hydrophobic or hydrophilic then only fluid diffusion occurs at the interface where the two fluids meet. A spacer structure 22 is maintained either on substrate 8 or 14. The spacer can be any thin or thick film of any material. The purpose of the spacers is to allow tiny air gaps between the substrates to maintain atmospheric pressure conditions on both sides of the fluidic plugs 24 and 20. Additionally hydrophobic coatings are maintained on the surfaces 27 and 28 to prevent fluids to wick to the surfaces. These coatings are patterned such that, the hydrophobic coating stops approximately 0.1–100 microns away from the through hole opening, giving rise to a hydrophyllic window opening that contributes to a fluid reservoir beyond the hole opening which prevents the meniscus becoming concave as evaporation proceeds.

Figure 2:
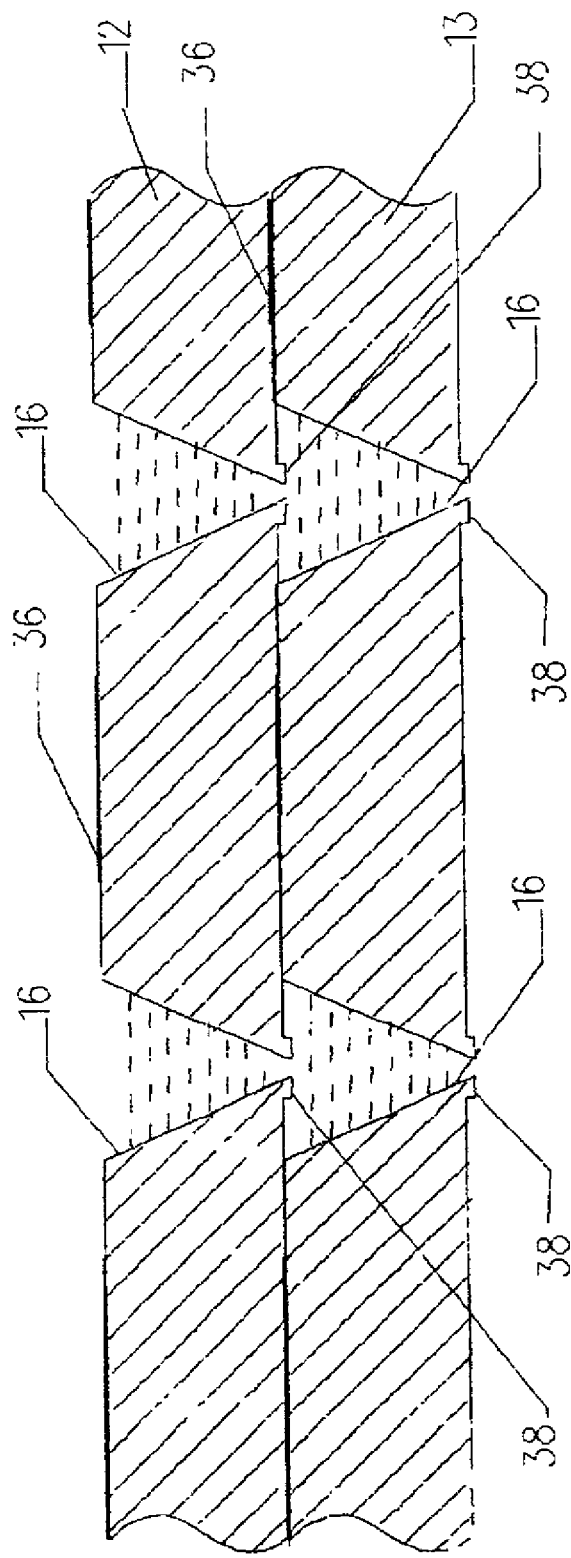
FIG. 2 is a cross sectional view of mixing fluids across two microfluidic through holes in two different substrates.

In an alternate embodiment in FIG. 2, a top substrate 12 having a plurality of through holes 16 having tapered walls are aligned with the through holes in a bottom substrate 13. The top substrate consists of etched through holes of straight or tapered walls. The bottom substrate also containes etched through holes of straight or tapered walls. The substrates have a coating of hydrophobic materials on the one or both sides 36. The hydrophobic window opening is larger than the through hole opening. This makes the fluid in the through hole to protrude out and cover the area up to the edge of the hydrophobic window. This enables the mixing of the two fluid meniscus despite the slow evaporation of the fluid through the through holes. In addition, one side of the through holes have a "collar," 38 which allows lowering of the meniscus of one fluid into the other fluid. The collar structure consists of etched raised rings, which are formed by removing the substrate material outside of the rings, leaving a raised platform around the through hole opening on one side of the substrate. Without this "collar ", after sufficient evaporation of the fluid, the fluid meniscus recedes into the through hole and at that point the two meniscus cannot meet each other. Without the meniscus touching each other, fluid would not be drawn into the second through hole. Both fluid transfer and fluid interface diffusion occur by contacting the two substrates filled with fluids in the through holes.

The present invention allows fluid transfer to the top substrate called fluid drawing, fluid transfer to the bottom substrate called fluid delivery and fluid interface diffusion called diffusional mixing. Therefore, this is an integrated platform for high throughput screening where a complicated and expensive dispenser is not needed. A large number of fluid array can be used where parallel fluid transfer and/or mixing occurs across the entire wafer. This allows building of a large library of fluids for the various purposes of combinatorial assay development, assay implementation, combinatorial chemical library synthesis, fluid storage and an environment for cell culturing.

The "collar" on the substrata can also make the top substrate self align with the bottom substrate. This makes positioning the top substrate very easy. In addition, the top substrate can be covered by a thin plastic layer such as a tape, to prevent evaporation of the fluid. The bottom through hole opening of the bottom substrate is much smaller compared to the top side that the evaporation would be minimized.

Gravitation effects are still applicable at the length scales of the above array. But surface properties and capillary action become comparable forces to gravity and fluids experience a resultant of all these forces. It should be noted that, the orientation of the substrates can be changed from horizontal to vertical and any angle in between. The phenomena and usage is applicable in any orientation and the reference to "upper" and "lower" is relative. Alternative forces can be generated by the use of vacuum, hydraulic pressure, acoustic energy and electrokinetics. The use of these is described henceforth.

Electric fields can be used to move the fluids from one substrate to another based on the electrokinetic phenomena as shown in FIGS. 3A–C. Substrate 52 has the though hole micro arrays 16. Electrodes 42 or an electrically conductive material cover a substantial portion of the through hole walls. These electrodes are all connected to power and can be programmed independently of the other electrodes. Hydrophobic coatings 36 are coated on both sides of both the substrates 52 and 58. The samples and reagents 24 are either dissolved in liquids, mixed in gels, or other conductive or non conductive polymer matrix, impregnated into porous gels, or coated on one side of one chip. The matrix composition could be simple fluids to multi component gels of interpenetrating network of an electroconductive polymer and a hydrophilic or hydrophobic gel. A substrate 58 that is similarly prepared to the substrate 52 is turned upside down with the smaller opening side 46 facing up. Both the substrates through holes 16 are filled with samples 24. The smaller openings 46 of both the top and bottom substrates 52 and 58 is aligned with each other and contacted together. This arrangement allows self aligning and penetration of the meniscus from each substrate. Electric fields or charge is applied by the electrodes 44 from a voltage or current source 50. The electric fields form a gradient across the through holes with closer field lines near the narrow part 46 of the substrates 52 and 58 and the field lines are farther apart at the wider part 48 of the substrates. This non uniform fields or field gradient sets up electrokinetic forces within the fluid and the fluid moves either up or down through the through holes depending on the polarity of the electric field, pH of the fluid and the zeta potential of the substrate materials. This motion facilitates the fluid dispensing, fluid withdrawal and fluid mixing, and fluid spotting on to well less plates. This enables the usage of multiple types of fluid samples to create a true 3-dimensional assay library or combinatorial library.

Both narrow and wide electrodes can be used for the electrokinetic fluid pumping. Electrodes 42 can be deposited on the substrate 52 or 58 by the various electronics manufacturing techniques such as sputtering, electron evaporation, thermal spraying, spin coating of metal inks, electrochemical and electroless deposition techniques. Patterning of the electrodes is done by lithography and wet and dry etching, silk screen printing, and electron beam writing. These manufacturing techniques are known to the skilled in the art of semiconductor or circuit board manufacturing. The metals of interest are gold, platinum, silver, chromium, aluminum, copper, tungsten and others that are patternable by the thin and thick film technologies.

Pressure Induced Dispensing

Figure 4:
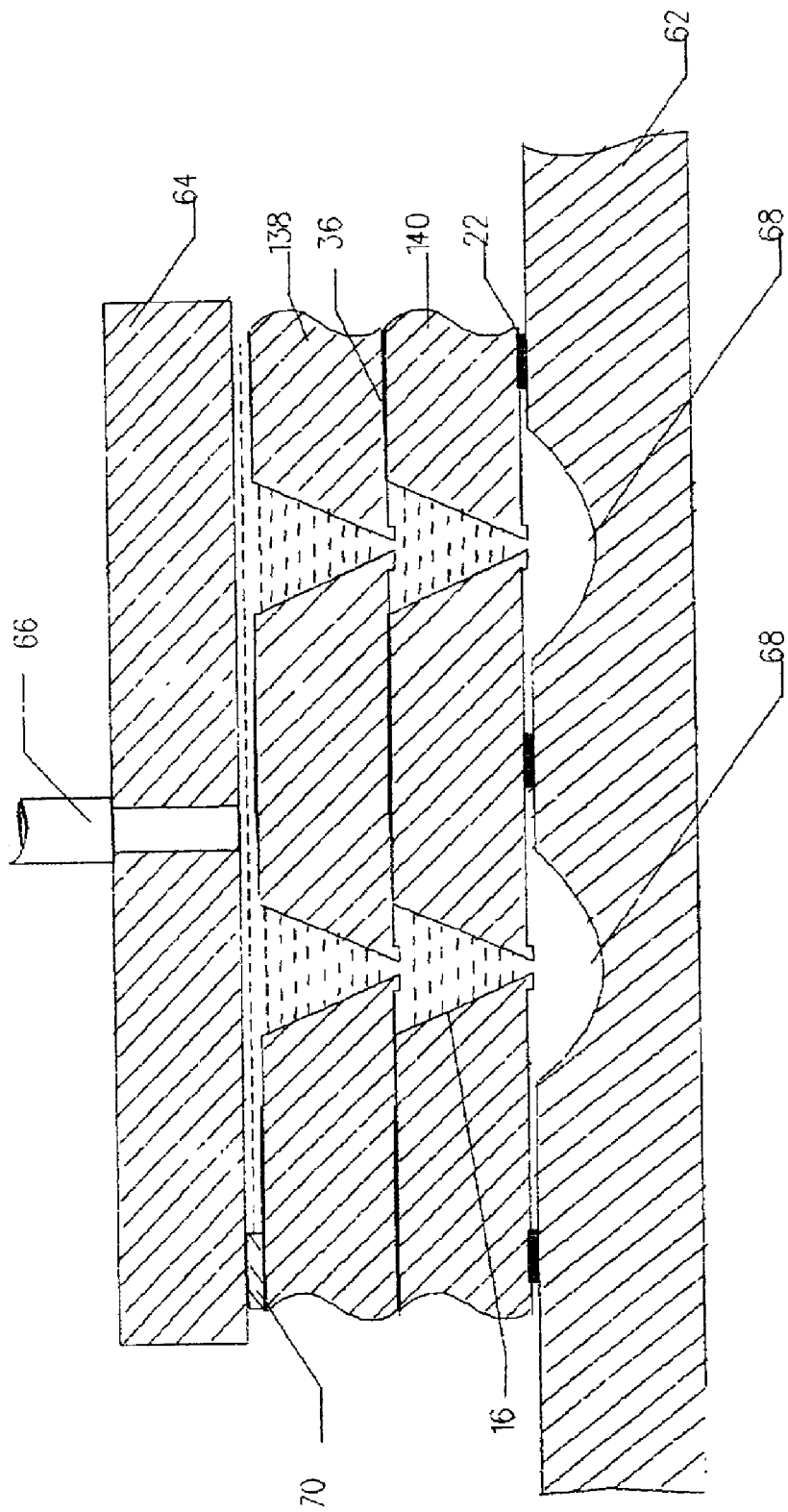
FIG. 4 is a cross sectional view of pushing the plug of fluid from two substrates into a microwell.

Embodiment in FIG. 4 shows the cross sectional view of using pressurized air, galvanized to load liquids into the array of microwells 68 for additional processing. The through holes 16 of substrates 138 and 140 are substantially aligned with one another and also with the microwells 68 disposed in substrate 62. A dispensing substrate 64 with an inlet 66 for air or liquid is used to push the fluid in the through holes 16 into the microwell 68. Fluid tight sealing is provided by a gasket 70 which prevents the liquid from escaping beyond the gasket.

Manufacturing Issues

The substrates 6, 8, 12, 13, 14, 52, 58, 62, 64, 138, 140 are of materials quartz, glass, silicon, and plastics of cross linked and non-cross linked structure. Some examples of the plastics are PMMA (polymethyl methacralate), polystyrene, PVC (poly vinyl chloride), PVDF (poly vinyl di fluoride), PDMS (poly di methyl siloxanes), and polyester, and nylons. The substrates are further undergone various chemical processes to generate the geometries and the surface conditions in the through holes and the rest of the surface of the substrates. Typical manufacturing sequence for the silicon-based substrates is as follows. Double-sided polished wafers of 100 micron to 1000 micron thickness are chosen. Silicon dioxide is grown on the silicon using thermal wet oxide, thermal dry oxide or other oxidation techniques known to the skilled in the art. Silicon nitride can be also used instead of the silicon dioxide. Other thin films such as photoresists, polysilicon, amorphous silicon, and metals can be used depending on the type of the substrate. A hole pattern is defined in the thin layer on the substrate using photolithography techniques.

Figure 9:
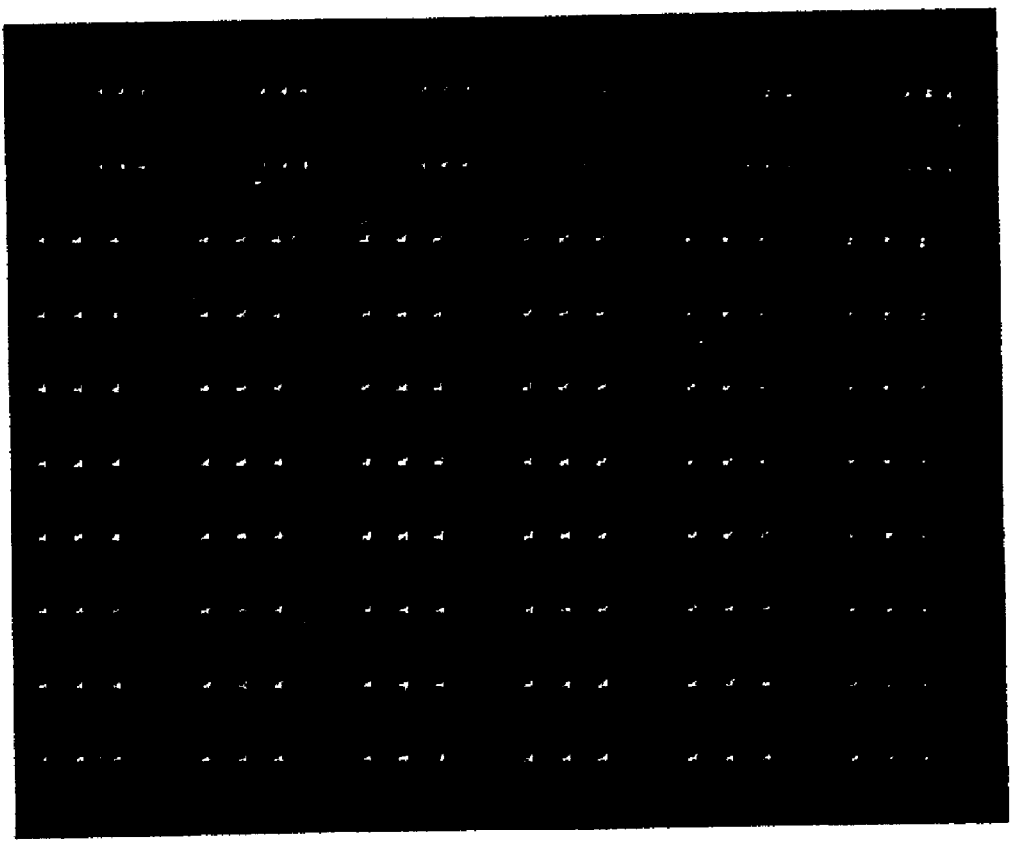
FIG. 9 shows the manufactured silicon subsrates with the array of through holes in the substrate.

Further etching of the thin layer is carried out to define windows in the thin layer. The exposed wafer surface is further etched using wet chemical etchants such as TMAH or KOH for a non straight though hole or plasma etching techniques are used for a straighter side wall profile of 16. The etching occurs all the way through the wafer substrate defining the through holes 16. The etching can define straight through holes, or truncated pyramid shaped holes, or curved shape holes. Further patterning to form structures such as 18, 38, 52 and 58 are carried out. The oxide layer is further removed and regrown to leave a thin layer of oxide on the inside surface of the through holes. Further chemical patterning is done to make the various surfaces hydrophobic or hydrophilic depending on the application. The coating materials are any of the polyimide, paralene, fluorocarbons, and silicones ranging in thickness from single monolayer of molecules to 5 microns thick. Contact printing, immersion coating, spin coating, UV curing, thermal curing are used to define the patterns. The hydrophobic coatings are defined slightly away from the outer edge of the through holes, since this enables the fluid body to protrude out making the mixing of the fluid meniscus easier. FIG. 9 shows the manufactured silicon substrate with 100 crystal surface with through holes etched along the 111 crystal orientation of the substrate.

Liquid Filling

Figure 5:
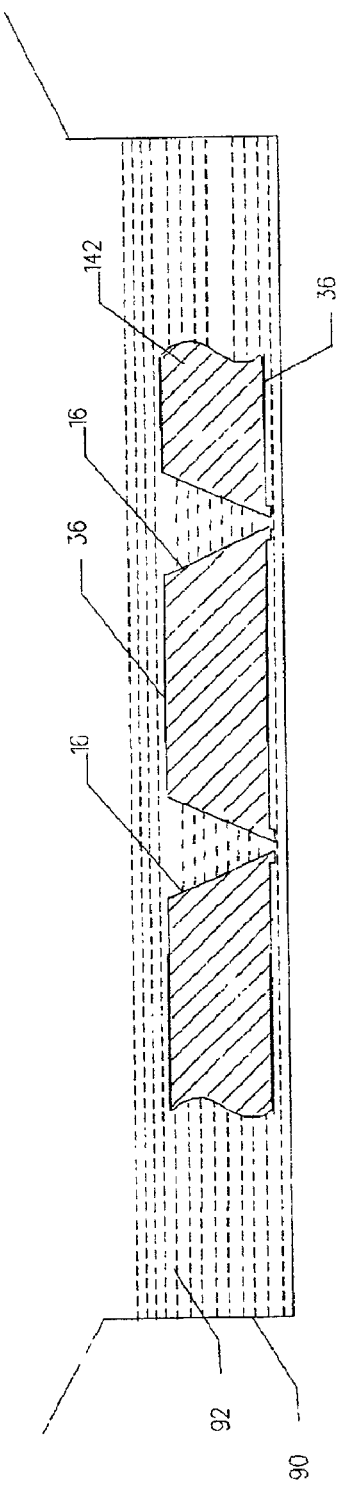
FIG. 5 shows the cross sectional view for filling fluid into the through holes by capillary action of the fluid.
Figure 6:
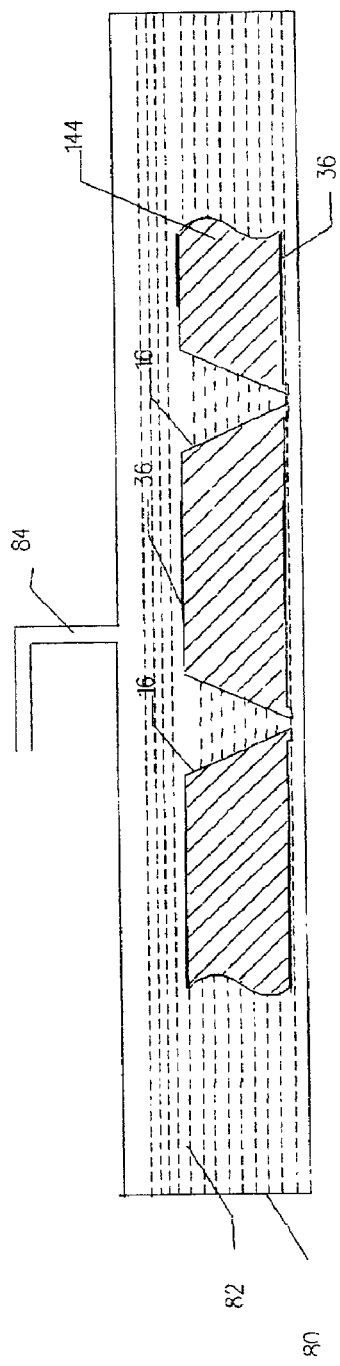
FIG. 6 is the cross sectional view of filling the through hole array by vacuum pressure induced on the top of the fluid with the substrate submerged in the fluid.

Liquid dispensing into the bottomless through hole microarray chips is carried out by the various means. One method is to use the capillary method described in FIG. 5. Substrate 142 with though hole 16 array is immersed in the sample liquid 92 contained by the container 90. Due to the capillary action fluid enters the though hole 16 array. This capillary action depends on the nature of the surface inside the through hole 16. Capillary action works only when this surface is hydrophilic. Glass, oxidized or bare silicon, plastics have hydrophilic surfaces. Hydrophilic coatings can also be applied to the inside surface of the through holes. Capillary action works from 10 micron size holes to 1 mm depending on the hydrophilicity. Hydrophobic coating 36 on the out side of the through hole on the substrate can be applied to make the fluid sample in the through hole not spread on to the surface of the substrate. If the inside surface of the through hole 16 is hydrophobic, capillary action does not work. Hydrophobic through hole surfaces are required when the fluid sample from this through hole needs to be transferred to a different substrate. In that case, submerged filling as shown in FIG. 6 can be used. The through holes 16 of the substrate 144 to be filled is submerged in the fluid sample liquid 82 contained in a container 80. Vacuum through the connection 84 is applied to the container 80. The air bubbles of the through holes move to the surface under the applied vacuum, with sample fluid 24 filling the volume of the through hole 16 of the substrate 144.

In another embodiment in FIG. 7A, after the microarray through holes of the substrate 148 filled using the above procedures in FIGS. 6 and 7, a scanning pneumatic micro blower 30 is used to blow off the liquid samples 25 that do not need transferring. The remaining liquids are further processed by stacking on a similar substrate 152 with different fluids 24 as shown in FIG. 7B.

Figures 8A, 8B:
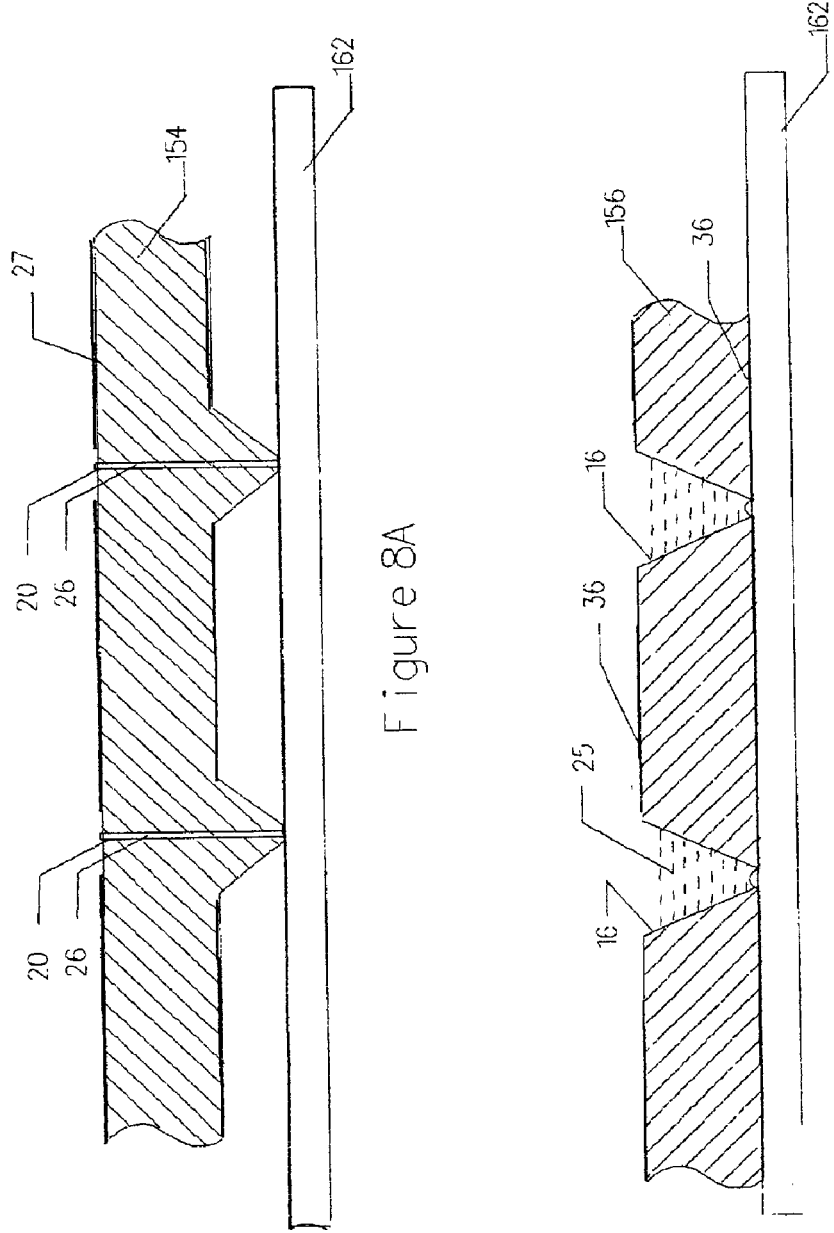
FIG. 8A shows the cross section of a through hole arrangement to spot array of fluid on to a second substrate.
FIG. 8B shows the cross section of the arrangement where the above spotted array substrate can be further processed to receive reagents from the top substrate

Another embodiment as shown in FIG. 8A shows the spotting technique on substrate 162 using a substrate 154 having the through holes 26 filled with liquid 20. This technique elegantly achieves the high density spotting without requiring any dispensing technique other than the capillary and electrokinetic means of transferring fluids to plane substrates. FIG. 8B shows an alternate embodiment of spotting on to planar substrate 162 using the substrate 156.

What is claimed is:

1. A microfluidic system comprising:
   a first substrate having at least one microfluidic through-hole between first and second surfaces of the first substrate, the through-hole having a cross-section sufficient to retain a liquid therein; and
   a first substrate having at least one peak protruding from the second surface of the first substrate, the at least one through-hole of the first substrate being in fluid communication with the tip of the at least one peak;
   a second substrate having at least one microfluidic through-hole in a predetermined proximate spaced position and alignment with the at least one microfluidic through-hole of the first substrate, the at least one through-hole of the second substrate operable to retain the liquid displaced from the at least one through-hole of the first substrate thereto.

2. The microfluidic system, as set forth in claim 1, further comprising means for displacing a liquid retained in the at least one through-hole of the first substrate to the at least one through-hole of the second substrate.

3. The microfluidic system, as set forth in claim 1, further comprising means for aligning the at least one microfluidic through-hole of the first and second substrates.

4. The microfluidic system, as set forth in claim 1, further comprising a physically driven force generated by meniscus contact between the liquids for displacing a liquid retained in the at least one through-hole of the first substrate to the at least one through-hole of the second substrate.

5. The microfluidic system, as set forth in claim 1, further comprising a chemically driven force generated by meniscus contact between the liquids for displacing a liquid retained in the at least one through-hole of the first substrate to the at least one through-hole of the second substrate.

6. The microfluidic system, as set forth in claim 1, further comprising a physically driven force generated by a pressure differential along the thickness of the substrates for displacing a liquid retained in the at least one through-hole of the first substrate to the at least one through-hole of the second substrate.

7. The microfluidic system, as set forth in claim 1, further comprising a physically driven force generated by an electrokinetic differential along the thickness of the substrates for displacing a liquid retained in the at least one through-hole of the first substrate to the at least one through-hole of the second substrate.

8. The microfluidic system, as set forth in claim 1, further comprising a spacer disposed between the first and second substrates and operable to maintain an air gap in the predetermined spaced position between the first and second substrates.

9. The microfluidic system, as set forth in claim 1, wherein the first and second substrates each further comprises hydrophobic upper and lower surfaces.

10. The microfluidic system, as set forth in claim 1, wherein the at least one microfluidic through-hole of the second substrate comprises a tapered inner wall.

11. The microfluidic system, as set forth in claim 1, wherein the at least one microfluidic through-hole of the first substrate comprises a tapered inner wall.

12. The microfluidic system, as set forth in claim 1, wherein the at least one microfluidic through-holes of the first and second substrates each comprises a tapered inner wall.

13. The microfluidic system, as set forth in claim 1, wherein the at least one peak of the first substrate is operable to be at least partially accommodated within the at least one microfluidic through-hole of the second substrate to make contact with the liquid retained therein.

14. The microfluidic system, as set forth in claim 1, wherein the first substrate further comprises a collar surrounding the opening of the at least one microfluidic through-hole in the second surface.

15. The microfluidic system, as set forth in claim 1, wherein the first and second substrates comprise a hydrophobic coating on the first and second surfaces thereof except for a predetermined distance from each through-hole opening.

16. The microfluidic system, as set forth in claim 15, wherein the first and second substrates further comprise a non-hydrophobic surface between the hydrophobic coating and the through-hole openings.

17. The microfluidic system, as set forth in claim 1, further comprising a plurality of microfluidic through-holes in each of the first and second substrates.

18. A microfluidic system comprising:
    a first substrate having an array of microfluidic through-holes having a first predetermined geometry between first and second surfaces of the first substrate, the through-holes operable to retain a liquid therein by physical and/or chemical fluidic forces;
    a first substrate having at least one peak protruding from the second surface of the first substrate, the at least one through-hole of the first substrate being in fluid communication with the tip of the at least one peak;
    a second substrate having an array of microfluidic through-holes having a second predetermined geometry and in a predetermined proximate spaced position and alignment with the microfluidic through-holes of the first substrate, the through-holes of the second substrate operable to receive and retain a liquid retained and then displaced from the through-holes of the first substrate to the through-holes of the second substrate, the through-holes operable to retain the liquid by physical and/or chemical fluidic forces; and
    an applied force operable to displace the liquid retained in the through-holes of the first substrate to the through-holes of the second substrate.

19. The microfluidic system, as set forth in claim 18, further comprising means for aligning the microfluidic through-holes of the first and second substrates.

20. The microfluidic system, as set forth in claim 18, wherein applied force comprises a force generated by meniscus contact between the liquids in the through-holes in the first and second substrates.

21. The microfluidic system, as set forth in claim 18, wherein the applied force comprises a physically driven force generated by a pressure differential along the thickness of the substrates.

22. The microfluidic system, as set forth in claim 18, wherein the applied force comprises a physically driven force generated by an electrokinetic differential along the thickness of the substrates.

23. The microfluidic system, as set forth in claim 18, further comprising a spacer disposed between the first and second substrates and operable to maintain an air gap in the predetermined spaced position between the first and second substrates.

24. The microfluidic system, as set forth in claim 18, wherein the first and second substrates each further comprises hydrophobic upper and lower surfaces.

25. The microfluidic system, as set forth in claim 18, wherein the first and second geometries of the through-holes are the same.

26. The microfluidic system, as set forth in claim 18, wherein the first and second geometries of the through-holes are different.

27. The microfluidic system, as set forth in claim 18, wherein the second predetermined geometries of the microfluidic through-holes of the second substrate comprises a tapered inner wall.

28. The microfluidic system, as set forth in claim 18, wherein the first and second predetermined geometries of the microfluidic through-holes of the first and second substrates comprise a tapered inner wall.

29. The microfluidic system, as set forth in claim 18, wherein the first and second predetermined geometries of the microfluidic through-holes of the first and second substrates comprise a conically tapered inner wall.

30. The microfluidic system, as set forth in claim 18, wherein the first and second predetermined geometries of the microfluidic through-holes of the first and second substrates comprise a pyramidally tapered inner wall.

31. The microfluidic system, as set forth in claim 18, wherein the microfluidic through-holes of the first substrate each reaching the second surface at a peak protruding therefrom.

32. The microfluidic system, as set forth in claim 29, wherein each peak of the first substrate is operable to be at least partially accommodated within the microfluidic through-hole of the second substrate to make contact with the liquid retained therein.

33. The microfluidic system, as set forth in claim 18, wherein the first substrate further comprises a collar surrounding the opening of each microfluidic through-hole and protruding beyond the second surface.

34. The microfluidic system, as set forth in 18, wherein the first and second substrates comprise a hydrophobic coating on the first and second surfaces thereof except for a predetermined distance from each through-hole opening.

35. The microfluidic system, as set forth in claim 18, further comprising a third substrate disposed adjacent the second substrate and having a plurality of microwells disposed in a surface of the substrate facing the second substrate, the microwells operable to receive the liquid displaced from the microfluidic through-holes of the first substrate to the microfluidic through-holes of the second substrate and then to the microwells.

36. The microfluidic system, as set forth in claim 35, further comprising a channel defined between the second and third substrates operable to guide the liquid from the microfluidic thorough-holes of the second substrate to the microwells in the third substrate.

37. The microfluidic system, as set forth in claim 18, wherein the through-holes in the first substrate are in in line alignment with the through-holes in the second substrate.

38. The microfluidic system, as set forth in claim 18, wherein the through-holes in the first substrate are in offset alignment with the through-holes in the second substrate.

39. The microfluidic system, as set forth in claim 38, further comprising a channel defined in the predetermined space between the first and second substrates and in fluid communication with selected through-holes of the first and second substrates.

40. A method of transferring liquids between first and second substrates, comprising:
    loading a first liquid into a plurality of microfluidic through-holes disposed in the first substrate, the first liquid being retained in the through-holes;
    loading a second liquid into a plurality of microfluidic through-holes disposed in the second substrate, the second liquid being retained in the through-holes; and transferring the first liquid in the first substrate into the through-holes of the second substrate induced by meniscus contact between the first and second liquids and an applied force.

41. The method, as set forth in claim 40, wherein transferring the first liquid comprises creating an electrical field differential across the first and second substrates.

42. The method, as set forth in claim 40, wherein transferring the first liquid comprises creating a pneumatic differential across the first and second substrates.

43. The method, as set forth in claim 40, further comprising transferring the liquid in the through-holes of the second substrate to microwells disposed in a third substrate.

44. The method, as set forth in claim 40, further comprising positioning the first and second substrates so that the through-holes therein are in alignment with one another.

45. The method, as set forth in claim 40, further comprising positioning the first and second substrates so that a fluid-conducting channel is formed between the first and second substrates, the channel being in fluid communication with at least selected ones of through-holes in the first and second substrates.

46. The method, as set forth in claim 40, wherein loading the through-holes of the first and second substrates comprises immersing the first and second substrates into the respective first and second liquids.

47. The method, as set forth in claim 46, wherein loading the through-holes of the first and second substrates comprises:
  immersing the first and second substrates into respective containers containing the respective first and second liquids; and
  evacuating gases from the respective containers.

48. A method comprising:
  loading a first test sample into a plurality of microfluidic through-holes disposed in the first substrate, the first test samples being retained in the through-holes;
  loading a reagent into a plurality of microfluidic through holes disposed in the second substrate, the reagent being retained in the through-holes; and
  transferring the reagent in the second substrate into the through-holes of the first substrate induced by an applied force;
  positioning and aligning a third substrate having a plurality of microfluidic through-holes with the microfluidic through-holes of the first substrate and forming a fluid conducting channel in fluid communication with the through-holes of the first and third substrates between the first and third substrates; and
  flushing the test sample reagent mixture in the through holes of the first substrate with a washing liquid introduced into the through-holes of the third substrate.

49. The method, as set forth in claim 48, wherein transferring the reagent comprises creating an electrical field differential across the first and second substrates.

50. The method, as set forth in claim 48, wherein transferring the reagent comprises creating a pneumatic differential across the first and second substrates.

51. The method, as set forth in claim 48, further comprising transferring the test sample and reagent in the through-holes of the first substrate to microwells disposed in a fourth substrate.

52. A method of preparing samples comprising:
  introducing an array of samples into a first substrate retained thereby by various fluid imbalance forces;
  positioning a second substrate adjacent the first substrate and receiving an array of spots of samples therefrom onto the second substrate;
  positioning a third substrate adjacent the second to further create another array of samples on the second substrate;
  repeating the above step with additional substrates to build a library of samples on the second substrate; and
  positioning and aligning the second substrate with the library of samples adjacent to an assay reagent substrate having an array of assay reagents.

53. The method, as set forth in claim 52, further comprising transferring the samples to the second substrate by applying an electrical field differential across the first and second substrates.

54. The method, a s set forth in claim 52, further comprising transferring the samples to the second substrate by a pneumatic differential across the first and second substrates.

55. The method, as set forth in claim 40, wherein, un-loading the through holes of the first and second substrates comprises blowing a gas jet against the through-holes.

* * * * *